United States Patent [19]

Kristiansen et al.

[11] 4,172,135
[45] Oct. 23, 1979

[54] BENZENEACETIC ACID ESTER DERIVATIVES

[75] Inventors: Odd Kristiansen, Möhlin; Peter Ackermann, Reinach; Jozef Drabek, Oberwil; Saleem Farooq, Ettingen; Laurenz Gsell, Füllinsdorf, all of Switzerland

[73] Assignee: Ciba-Geigy Corporation, Ardsley, N.Y.

[21] Appl. No.: 925,342

[22] Filed: Jul. 17, 1978

[30] Foreign Application Priority Data

Jul. 20, 1977 [CH] Switzerland .......................... 8999/77
Dec. 7, 1977 [CH] Switzerland ........................ 15003/77
May 26, 1978 [CH] Switzerland .......................... 5777/78

[51] Int. Cl.² ................... C07D 213/63; A61K 31/44
[52] U.S. Cl. ..................................... 424/263; 546/301
[58] Field of Search ......................... 546/301; 424/263

[56] References Cited

U.S. PATENT DOCUMENTS

| | | | |
|---|---|---|---|
| 4,031,233 | 6/1977 | Kathawala | 424/273 R |
| 4,039,680 | 8/1977 | Fujimoto et al. | 424/275 |
| 4,058,622 | 11/1977 | Fujimoto et al. | 424/308 |

*Primary Examiner*—Alan L. Rotman
*Attorney, Agent, or Firm*—Harry Falber

[57] ABSTRACT

Phenyl acetates of the formula

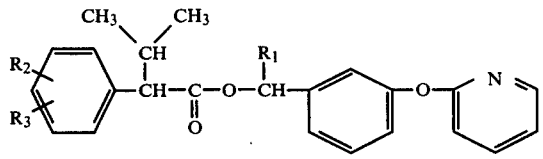

wherein
$R_1$ represents hydrogen, cyano, ethynyl or methyl, and
$R_2$ and $R_3$ each represent hydrogen, halogen, $C_1$–$C_4$-alkyl or $C_1$–$C_4$-alkoxy, processes for producing them, and their use in combating pests.

8 Claims, No Drawings

BENZENEACETIC ACID ESTER DERIVATIVES

The present invention relates to phenyl acetates and to salts thereof with inorganic and organic acids, to processes for producing them, and to their use in combating pests.

The said phenyl acetates have the formula $$\text{(I)}$$

wherein
- $R_1$ represents hydrogen, cyano, ethynyl or methyl, and
- $R_2$ and $R_3$ each represent hydrogen, halogen, $C_1$–$C_4$-alkyl or $C_1$–$C_4$-alkoxy.

Suitable for forming salts are inorganic acids such as HCl, $H_2SO_4$, HBr and $H_3PO_4$, and organic acids such as saturated and unsaturated mono-, di- and tricarboxylic acids, e.g. formic acid, acetic acid, oxalic acid, phthalic acid, succinic acid and citric acid.

By halogen denoted by $R_2$ and $R_3$ are meant fluorine, chlorine, bromine and iodine, particularly however chlorine.

The alkyl or alkoxy groups in the case of $R_2$ and $R_3$ can be straight-chain or branched-chain. Examples of such groups are, inter alia: methyl, methoxy, ethyl, ethoxy, propyl, propoxy, isopropyl, isopropoxy, n-butyl, n-butoxy and i-, sec- or tert-butyl.

Compounds of the formula I preferred on account of their effectiveness are those wherein $R_1$ represents cyano, and $R_2$ and $R_3$ each represent hydrogen or chlorine.

The compounds of the formula I are produced by methods known per se, for example as follows:

(1) (II) + (III) $\xrightarrow{\text{acid-binding agent}}$ I (2) (IV) + (V) $\xrightarrow{\text{acid-binding agent}}$ I (3) (II) + (V) $\xrightarrow{\text{water-binding agent}}$ I (4) (VI) + (V) $\xrightarrow{-ROH}$ I In the formulae II to VI, $R_1$, $R_2$ and $R_3$ have the meanings given under the formula I.

In the formulae III and IV, X represents a halogen atom, especially chlorine or bromine; and in the formula VI, R represents $C_1$–$C_4$-alkyl, particularly methyl or ethyl.

Suitable acid-binding agents for the processes 1 and 2 are in particular tertiary amines, such as trialkylamine and pyridine, also hydroxides, oxides, carbonates and bicarbonates of alkali metals and alkaline-earth metals, and also alkali metal alkoholates, e.g. potassium-t.-butylate and sodium methylate. The water-binding agent used for the process 3 can be, for example, dicyclohexylcarbodiimide. The processes 1 to 4 are performed at a reaction temperature of between −10 and 120° C. generally between 20° and 80° C., at normal or elevated pressure and preferably in an inert solvent or diluent. Suitable solvents or diluents are, for example, ethers and ethereal compounds such as diethyl ether, dipropyl ether, dioxane, dimethoxyethane and tetrahydrofuran; amides such as N,N-dialkylated carboxylic acid amides; aliphatic, aromatic and also halogenated hydrocarbons, in particular benzene, toluene, xylene, chloroform and chlorobenzene; nitriles such as acetonitrile; dimethylsulphoxide and ketones such as acetone and methyl ethyl ketone.

The starting materials of the formulae II, IV and VI are known, whereas the starting materials of the formulae III and V are novel. All these starting materials can be produced by methods analogous to known methods.

Unless homogeneous optically active acting materials are used in the production process, the compounds of the formula I are obtained as mixtures of various optically active isomers. The different isomeric mixtures can be separated by known methods into the individual isomers. By the term 'compound of the formula I' are meant both the individual isomers and mixtures thereof.

The compounds of the formula I are suitable for combating various animal and plant pests. They are suitable in particular for combating insects and phytopathogenic mites and ticks, e.g. of the orders Lepidoptera, Coleoptera, Homoptera, Heteroptera, Diptera, Acarina, Thysanoptera, Orthoptera, Anoplura, Siphonoptera, Mallophaga, Thysanura, Isoptera, Psocoptera and Hymenoptera.

Compounds of the formula I are especially suitable for combating insects which damage plants, particularly insects which damage plants by eating, in crops of ornamental plants and useful plants, especially in cotton crops, (.e.g. against *Spodoptera littoralis* and *Heliothis virescens*) and in crops of vegetables (e.g. against *Leptinotarsa decemlineata* and *Myzus persicae*). The active substances of the formula I also exhibit a very favourable action against flies, such as *Musca domestica,* and against mosquito larvae.

The acaricidal and insecticidal action can be substantially broadened and adapted to suit given circumstances by the addition of other insecticides and/or acaricides. Suitable additives are, for example, organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances which have a synergistic or intensifying effect. Examples of such compounds are, inter alia, piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-octylsulphonyl)-propyl)-benzene.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:
solid preparations: dusts, scattering agents, granules (coated granules, impregnated granules and homogeneous granules);
liquid preparations:
(a) water-dispersible concentrates of active substance: wettable powders, pastes or emulsions;
(b) solutions.

The content of active substance in the compositions described is between 0.1 and 95%, it is to be mentioned in this respect that with application from an aeroplane, or by other suitable devices, concentrations of up to 99.5% or even the pure active substance can be used.

The active substances of the formula I can be formulated for example as follows (parts are by weight):

DUSTS

The following substances are used to produce (a) a 5% dust and (b) a 2% dust:

(a)

5 parts of active substance, and
95 parts of talcum;

(b)

2 parts of active substance,
1 part of highly dispersed silicic acid, and
97 parts of talcum.

The active substance is mixed and ground with the carriers.

GRANULATE

The following ingredients are used to produce a 5% granulate:
5 parts of active substance
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone, and the polyethylene glycol and cetyl polyglycol ether are then added. The solution obtained is sprayed onto kaolin and the acetone is subsequently evaporated off in vacuo.

WETTABLE POWDERS

The following constituents are used to produce (a) a 40%, (b) and (c) a 25%, and (d) 10% wettable powder:

(a)

40 parts of active substance,
5 parts of sodium lignin sulphonate,
1 part of sodium dibutyl-naphthalene sulphonate, and
54 parts of silicic acid;

(b)

25 parts of active substance,
4.5 parts of calcium lignin in sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk, and
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr, and
46 parts of kaolin;

(d)

10 parts of active substance,
3 parts of a mixture of the sodium salts of saturated fatty alcohol sulphates,
5 parts of naphthalenesulphonic acid/formaldehyde condensate, and
82 parts of kaolin.

The active substance is intimately mixed in suitable mixers with the additives, and the mixture is then ground in the appropriate mills and rollers to obtain wettable powders which can be diluted with water to give suspensions of the desired concentration.

EMULSIFIABLE CONCENTRATES

The following substances are used to produce (a) a 10%, (b) a 25% and (c) a 50% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide, and
43.2 parts of xylene;

(b)

25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene;

(c)

50 parts of active substance,
4.2 parts of tributylphenol-polyglycol ether,
5.8 parts of calcium-dodecylbenzenesulphonate,
20 parts of cyclohexanone, and
20 parts of xylene.

Emulsions of the concentration required can be prepared from these concentrates by dilution with water.

SPRAY

The following constituents are used to produce (a) a 5% spray and (b) a 95% spray:

(a)

5 parts of active substance,
1 part of epichlorohydrin, and
94 parts of ligroin (boiling limites 160°–190° C.);

(b)

95 parts of active substance, and
5 parts of epichlorohydrin.

The invention is further illustrated by the following Examples.

EXAMPLE 1

Production of α,α-p-chlorophenyl-isopropylacetic acid α'-cyano-3'-pyridyl-2'-oxybenzyl ester 7.5 g of α,α-p-chlorophenyl-isopropylacetic acid chloride in 10 ml of abs. toluene is added dropwise at 5° C. to a solution of 7.5 g of α-cyano-3-(pyridyl-2'-oxy)-benzyl alcohol and 2.7 g of pyridine in 100 ml of abs. toluene. The reaction mixture is stirred for 5hours at room temperature, and is then poured into ice water. The organic layer is washed with 3% hydrochloric acid, with water, with 3% sodium bicarbonate solution and again with water. Drying over sodium sulphate and removal of the toluene by distillation yield the compound of the formula

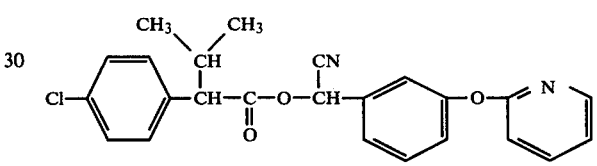

as a viscous liquid having a refractive index of $n_D^{20°} = 1.5656$.

The following compounds are produced in an analogous manner:

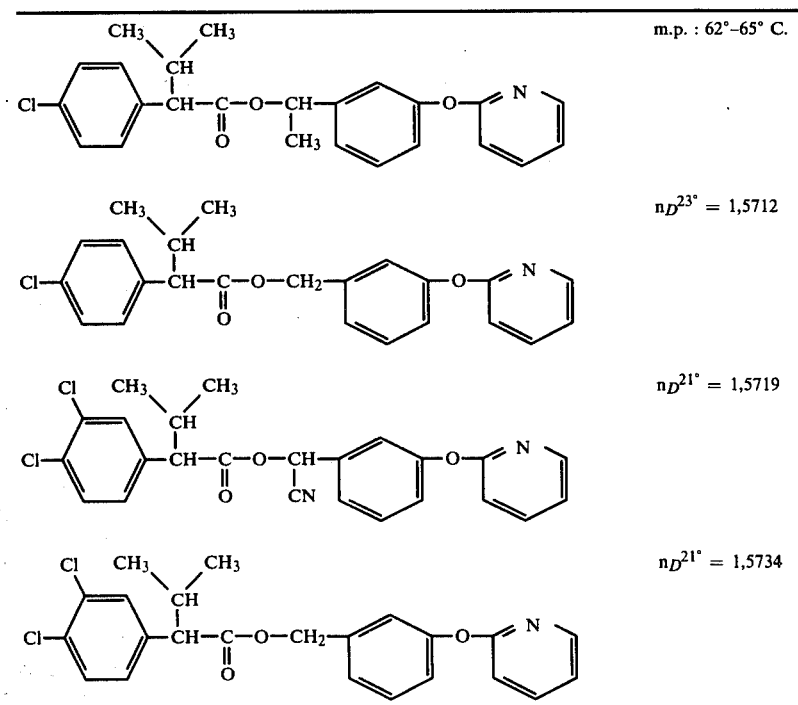

m.p. : 62°–65° C.

$n_D^{23°} = 1,5712$ $n_D^{21°} = 1,5719$ $n_D^{21°} = 1,5734$

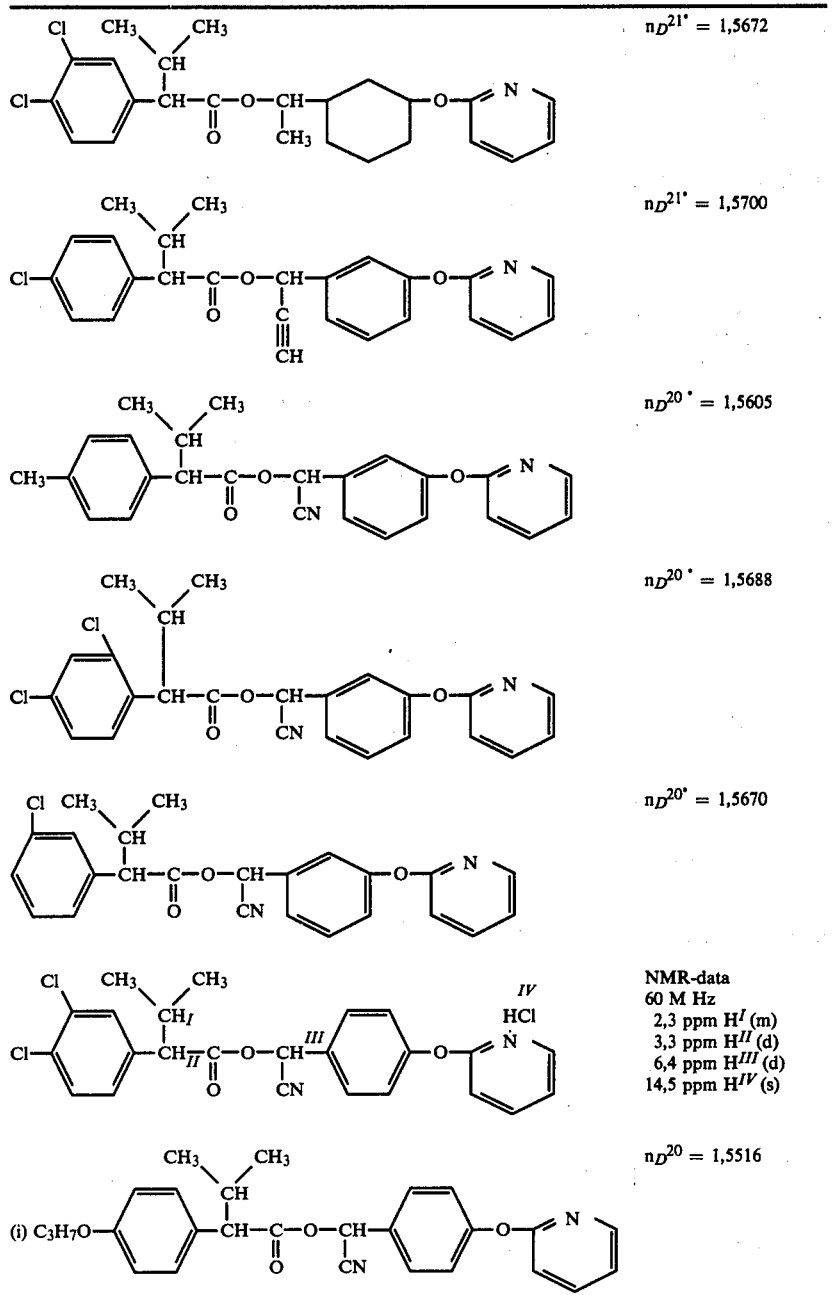

EXAMPLE 2

(A) Insecticidal stomach-poison action

Cotton plants were sprayed with a 0.05% aqueous emulsion of the active substance (obtained from a 10% emulsifiable concentrate).

After the coating had dried, $L_3$ larvae of *Spodoptera littoralis* and of *Heliothis virescens* were placed onto the cotton plants. The test was carried out at 24° C. with 60% relative humidity.

Compounds according to Example 1 exhibited in the above test a good insecticidal stomach poison action against *Spodoptera littoralis* and *Heliothis virescens* larvae.

EXAMPLE 3

Action against *Chilo suppressalis*

Rice plants of the variety Caloro were placed six plants per pot in plastic pots having an upper diameter of 17 cm, and grown to a height of about 60 cm. Infestation with *Chilo suppressalis* larvae ($L_1$: 3–4 mm long) was carried out 2 days after application of the active substance in granular form (amount applied = 8 kg of active substance per hectare) to the paddy water. An evaluation of the insecticidal action was made 10 days after application of the granules.

Compounds according to Example 1 were effective in the above test against *Chilo suppressalis*.

EXAMPLE 4

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 to 7 days, by examination under a binocular microscope, of the living larvae and of the dead larvae, adults and eggs, and the results were expressed as percentages. The treated plants were kept during the "holding time" in greenhouse compartments at 25° C.

Compounds according to Example 1 were effective in the above test against adults, larvae and eggs of *Tetranychus urticae*.

EXAMPLE 5

Action against ticks (A) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(b) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of Rhipicephalus bursa and against sensitive and OP-resistant larvae, respectively, of *Boophilus microplus*.

We claim:

1. A compound of the formula

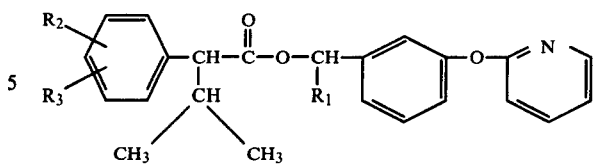

wherein
$R_1$ represents hydrogen, cyano, ethynyl or methyl, and
$R_2$ and $R_3$ each represent hydrogen, halogen, $C_1-C_4$-alkyl or $C_1-C_4$-alkoxy.

2. A compound according to claim 1, wherein $R_1$ represents cyano, and $R_2$ and $R_3$ each represent hydrogen or chlorine.

3. The compound according to claim 2 of the formula

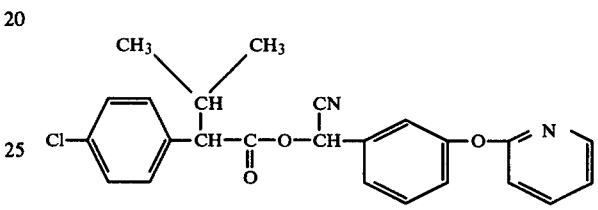

4. The compound according to claim 2 of the formula

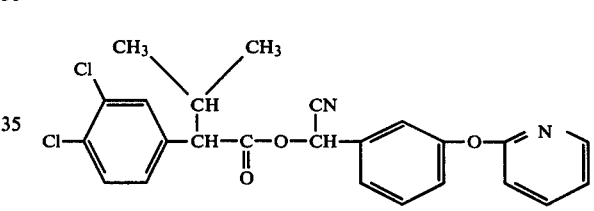

5. The compound according to claim 2 of the formula

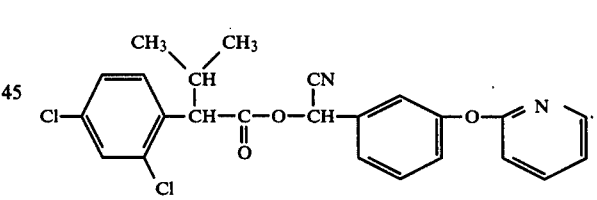

6. A pesticidal composition which comprises an effective amount of a compound according to claim 1 as active ingredient, and suitable carriers and/or other additives.

7. A method of combating various animal and plant pests at a locus an effective amount of, which method comprises applying to the locus a compound as claimed in claim 1.

8. A method according to claim 7, wherein the pests are of the class Insecta or of the order Acarina.

* * * * *